United States Patent [19]

Apeler et al.

[11] Patent Number: 5,707,831

[45] Date of Patent: Jan. 13, 1998

[54] PROCESS FOR PREPARING RECOMBINANT APROTININ AND RECOMBINANT APROTININ VARIANTS HAVING THE NATURAL N-TERMINAL SEQUENCE

[75] Inventors: Heiner Apeler; Jürgen Beunink, both of Wuppertal; Michael Dörschug, Heiligenhaus; Uwe Gottschalk, Velbert, all of Germany

[73] Assignee: Bayer Aktiengesellschaft, Leverkusen, Germany

[21] Appl. No.: 439,585

[22] Filed: May 11, 1995

[30] Foreign Application Priority Data

May 18, 1994 [DE] Germany .................... 44 17 353.9

[51] Int. Cl.$^6$ ........................ C12P 21/06; C12N 15/00
[52] U.S. Cl. ........................ 435/69.2; 435/320.1
[58] Field of Search ........................ 435/320.1, 69.2; 530/324

[56] References Cited

U.S. PATENT DOCUMENTS

| | | | |
|---|---|---|---|
| 4,595,674 | 6/1986 | Tschesche et al. | 514/9 |
| 5,118,668 | 6/1992 | Auerswald et al. | 514/12 |
| 5,164,482 | 11/1992 | Ebbers et al. | 530/324 |
| 5,258,302 | 11/1993 | Vedvick et al. | 435/254.23 |
| 5,395,922 | 3/1995 | Bjorn et al. | 530/350 |
| 5,591,603 | 1/1997 | Bjorn et al. | 435/69.2 |

FOREIGN PATENT DOCUMENTS

| | | |
|---|---|---|
| 0419878 | of 0000 | European Pat. Off. . |
| 8901968 | 3/1989 | WIPO . |
| 8902463 | 3/1989 | WIPO . |

OTHER PUBLICATIONS

W. Gebhard et al., Barret and Salvesen eds. Elsevier Science Publ. BV 375–376, 378 (1986).

Wlodawer et al., J. Mol. Biol. 198 (3), 469–480, 1987.

Wagner et al., J. Mol. Biol. 196 (1), 227–231, 1987.

Berndt et al., Biochemistry 32 (17), 4564–4570, 1993.

Bistrup et al., Lancet 1, 366–367, 1988.

Auerswald et al., Biol. Chem. Hoppe Seyler 369, 27–35, 1988.

A.J. Brake, Methods in Enzymology 185, 408–421, 1990.

Das et al., Biotechn. Progress 3, 43–48, 1987.

Taylor et al, Nucl. Acids Res. 13, 8765–8785, 1985.

Kurjan und Herskowitz, Cell 30, 933–943, 1982.

Yarger et al., Mol. Cell. Biol. 6, 1095–1101, 1986.

Marks et al., 1986, Journal of Biological Chemistry, 261 (16), 7115–7118.

*Primary Examiner*—Rebecca E. Prouty
*Assistant Examiner*—Lisa J. Hobbs
*Attorney, Agent, or Firm*—Sprung Kramer Schaefer & Briscoe

[57] ABSTRACT

The invention relates to a process for preparing recombinant aprotinin and recombinant aprotinin variants having the natural N-terminal sequence, with the recombinant aprotinin and/or the recombinant aprotinin variants being present as homogeneously processed, secreted proteins.

2 Claims, 2 Drawing Sheets

PROCESS FOR PREPARING RECOMBINANT APROTININ AND RECOMBINANT APROTININ VARIANTS HAVING THE NATURAL N-TERMINAL SEQUENCE

The invention relates to a process for preparing recombinant aprotinin and recombinant aprotinin variants having the natural N-terminal sequence, with the recombinant aprotinin and/or the recombinant aprotinin variants being present as homogeneously processed, secreted proteins.

Aprotinin, which is also termed "bovine pancreatic trypsin inhibitor" (BPTI), belongs to the family of Kunitz-type inhibitors. The spectrum of serine proteases which can be inhibited includes, for example, trypsin, chymotrypsin, plasmin and plasma kallikrein (W. Gebhard, H. Tschesche and H. Fritz, Proteinase Inhibitors, Barrett and Salvesen (eds.), Elsevier Science Publ. BV 375–387, 1986).

Aprotinin consists of 58 amino acids. The 3-dimensional structure of the protein was elucidated using X-ray structural analysis and NMR spectroscopy (Wlodawer et al., J. Mol. Biol. 198 (3), 469–480, 1987; Wagner et al., J. Mol. Biol. 196 (1), 227–231, 1987; Berndt et at., Biochemistry 32 (17), 4564–4570, 1993).

Natural aprotinin is employed under the trade name Trasylol for treating pancreatitis. For some time now, Trasylol has also been used in open heart surgery once clinical studies had demonstrated that treatment with aprotinin significantly reduces blood loss in operations of this type and leads to a reduction in post-operative bleeding (Bistrup et al., Lancet 1, 366–367, 1988).

Aprotinin variants having a different amino acid at position 15 exhibit a strong inhibitory activity towards the elastases from pancreas and leucocytes and the protease cathepsin G (Tschesche et al., U.S. Pat. No. 4,595,674).

Aprotinin variants having the amino acid arginine at position 15 differ from the natural aprotinin in having a higher affinity for plasma kallikrein.

The expression of recombinant aprotinins has been described for E. coli K 12 (Auerswald et at., Biol. Chem. Hoppe Seyler 369, 27–35, 1988) and for yeast (EP 0 419 878).

In the yeast system, signal sequences of secretory yeast proteins, such as, for example, the signal sequence of the alpha-mating factor, have been linked to the N terminus of the aprotinin variants. The processing of the prepro-alpha factor/aprotinin fusion proteins requires the activity of two different proteolytic enzymes. The so-called signal peptidase, which is located in the endoplasmic reticulum, initially cleaves the fusion protein between amino acids 19 and 20. The resulting pro-alpha factor/aprotinin—which is glycosylated in the pro region—is then cleaved by an endoproteinase which specifically recognizes the dibasic amino acid pair Lys-Arg. This endoproteinase is the product of the KexII gene. The cleavage by the KexII protease thus results in the liberation and secretion of the aprotinin (A. J. Brake, Methods in Enzymology 185, 408–421, 1990; Das et at., Biotechn. Progress 3, 43–48, 1987).

However, in the case of the recombinant aprotinin and aprotinin variants, it was found that the KexII protease was not able to cleave off aprotinins having the natural N-terminal sequence "Arg-Pro-Asp". It was not possible to express a secreted aprotinin which was processed uniformly and correctly.

It was possible to solve this processing problem (EP 0 419 878) by altering the N-terminal sequence of the aprotinin either by deleting the amino acid proline at position 2 or by inserting the amino acids alanine and glutamine at positions −2 and −1. A high percentage of the aprotinins resulting from these modifications were correctly processed.

However, it is not desirable to alter the N-terminal sequence of aprotinin or the aprotinin variants in order to achieve correct processing in the yeast system since any of the N-terminally modified aprotinins could trigger an immune response.

The object of the invention is, therefore, to make available a process for preparing recombinant aprotinin, or recombinant aprotinin variants, having the natural N-terminal sequence "Arg-Pro-Asp", with the recombinant aprotinin and/or the recombinant aprotinin variants being present as homogeneously processed, secreted proteins.

Surprisingly, it was possible to achieve this object by completely deleting the alpha factor pro sequence from the prepro-alpha factor/aprotinin fusion construct. In this case, therefore, the alpha factor pre sequence is linked directly to the aprotinin sequence. The processing of this construct only requires the signal peptidase. A very high percentage of the recombinant aprotinin and/or the recombinant aprotinin variants is correctly processed and secreted into the medium. The "classical" route of secreting proteins in the yeast system, which requires the activity of the KexII protease, is not involved when using constructs having a deleted alpha factor pro sequence, as described in this invention.

WO 89/01968 also described a process which is based on the signal sequence of the alpha-mating factor and which allows aprotinin having a natural N terminus to be expressed in the yeast system. However, since this process evidently makes use of the proteolytic activity of the KexII protease, it does not appear suitable for preparing recombinant aprotinin and aprotinin variants having a correctly processed, natural N-terminal sequence.

The methods employed in the course of cloning, fermenting and purifying recombinant aprotinin, and the recombinant aprotinin variants, having the natural N-terminal sequence are given below.

Methods

Enzymes

The enzymes employed (restriction endonucleases, calf intestinal alkaline phosphatase, T4 polynucleotide kinase and T4 DNA ligase) were purchased from Boehringer Mannheim and GIBCO-BRL and used in accordance with the manufacturer's instructions.

Molecular Biological Techniques

Routine cloning procedures, such as the isolation of plasmid DNA from E. coli (so-called minipreps) and the transformation of E. coli with plasmid DNA, were carried out in accordance with Sambrook et al. (Molecular cloning, Cold Spring Harbor, 1989). The E. coli strain SURE® (Stratagene) was the principal host organism employed for transformations. Quiagen columns (Diagen) were used for isolating larger quantities of plasmid DNA. Jetsorb was used in accordance with the manufacturer's (Genomed) instructions for extracting DNA fragments from agarose gels.

Oligonucleotides for site-directed mutagenesis (deletion of the alpha factor pro sequence) and primers for sequencing were prepared using a 380 A DNA synthesizer from Applied Biosystems. The mutagenesis experiments were carried out in accordance with a method of Eckstein (Taylor et al., Nucl. Acids Res. 13, 8764–8785, 1985) using a kit from Amersham-Buchler (oligonucleotide-directed in-vitro mutagenesis system, version 2.1). All vector constructions and mutagenesis experiments were confirmed by single-strand or double-strand DNA sequencing. A kit from US Biochemical Corporation was employed for this purpose (Sequenase, version 2.0).

Transformation of *Saccharomyces cerevisiae*

Yeast cells, for example strain SC125A (MATa, ura3–52, suc2), were grown in 10 ml of YEPD (2% glucose; 2% peptone; 1% Difco yeast extract) and harvested at an $O.D._{600nm}$ of from 0.6 to 0.8. The cells were washed with 5 ml of solution A (1M sorbitol; 10 mM bicine, pH 8.35; 3% ethylene glycol), resuspended in 0.2 ml of solution A, and stored at −70° C.

Plasmid DNA (5 μg) and carrier DNA (50 μg of herring sperm DNA) were added to the frozen cells. The cells were then thawed by shaking at 37° C. for 5 min. After 1.5 ml of solution B (40% PEG 1000; 200 mM bicine, pH 8.35) had been added, the cells were incubated at 30° C. for 60 min, washed with 1.5 ml of solution C (0.15M NaCl; 10 mM bicine, pH 8.35) and resuspended in 100 μl of solution C. They were then plated out on a selective medium containing 2% agar. Transformants were obtained after incubating for 3 days at 30° C.

Fermentation of the Yeast Cells

Nutrient Solutions

The following nutrient solutions were used for fermenting yeast cells for the purpose of expressing aprotinin, or aprotinin variants, having the correct N-terminal amino acid sequence:

| Ingredient | Nutrient solution | |
|---|---|---|
| | SD2 | Sc6 |
| Bacto yeast nitrogen base | 6.7 g/l | — |
| Difco yeast extract | — | 20.0 g/l |
| Glucose | 20.0 g/l | 5.0 g/l |
| $KH_2PO_4$ | 6.7 g/l | 1.4 g/l |
| $(NH_4)_2SO_4$ | — | 2.0 g/l |
| $MgSO_4 \times 7 H_2O$ | — | 0.5 g/l |
| Anti-foaming agent PPG 2000 | — | 0.1 g/l |

The ingredients were mixed in demineralized water and the pH was adjusted to 5.5. The solution was sterilized at 121° C. for 20 min. Glucose was dissolved in ⅕ of the required volume of demineralized water and this solution was sterilized separately; it was then added to the rest of the nutrient solution once it had cooled.

Strain Stocks

Strain stocks of all the yeast transformants were laid down by filling storage vials with 2 ml aliquots of a preculture and storing them in liquid nitrogen.

Precultures

The preculture fermentations were carried out in 1 litre shake flasks which were filled with 200 ml of SD2 nutrient solution. The flasks were inoculated with a strain stock or with a single colony from an SD2 agar plate. The cultures were incubated, while being continuously shaken, at from 26° to 30° C. for from 2 to 3 days.

Main Culture Fermentations

The main culture fermentations were carded out in Sc6 nutrient solution using 10 litre stirred-tank fermenters. These were inoculated with from 3 to 5% by volume of a preculture, with the biomass from the preculture being centrifuged down and resuspended in Sc6 medium prior to inoculation. The fermentation conditions for the 10 litre main culture were as follows:

| Temperature | 26–30° C. |
|---|---|
| Rate of stirrer revolution | 600 rpm |
| Aeration rate | 0.5 vvm |
| pH set point | 5.5 (correction with 5 N NaOH and 5 N $H_2SO_4$) |

Once they had been fermented for 5 hours, the cultures were fed continuously with glucose and yeast extract. The feeding rate was regulated using the respiratory quotient (RQ value) of the culture. The RQ set point was 1.0. The feed solution had the following composition:

| Glucose | 500 g/l |
|---|---|
| Difco yeast extract | 75 g/l |

The constituents were dissolved separately in demineralized water and sterilized at 121° C. for 20 min. The two solutions were combined once they had been cooled.

When the inducible Gal10 promoter, or a derivative of the Gal10 promoter, was used, induction was effected by changing the carbohydrate in the feed solution from glucose (500 g/l) to galaclose (500 g/l). After that, the RQ value was no longer used to regulate the feeding rate. The feeding rate was adjusted manually to double the feeding rate at the time of the induction. The Gal10 promoter was normally induced after a fermentation period of about 48 hours.

Cell Harvest

After the fermentation was complete (from 80 to 120 hours), the contents of the fermenter were cooled down to from 10° to 15° C. and the yeast cells were separated out of the culture broth by standard centrifugation techniques (e.g. bucket centrifuge) or using cross-flow microfiltration (e.g. Filtron Minisette system). If necessary, the cells were washed and the culture broth was sterilized by filtration. When the heterologous protein was secreted, the product was purified from the cell-free culture broth; when the expression was intracellular, the biomass was used for purification.

Analytical Methods

N-terminal sequence determinations, amino acid analyses and the elastase and trypsin inhibition tests were carded out as described in U.S. Pat. No. 5,164,482.

The invention is explained in more detail by the following examples, figures and sequence information:

EXAMPLES

Example 1

Preparation of a Yeast Expression Vector for Secreting Recombinant Arg-15 Aprotinin having the Natural N-terminal Sequence "Arg-Pro-Asp"

Figure 1:
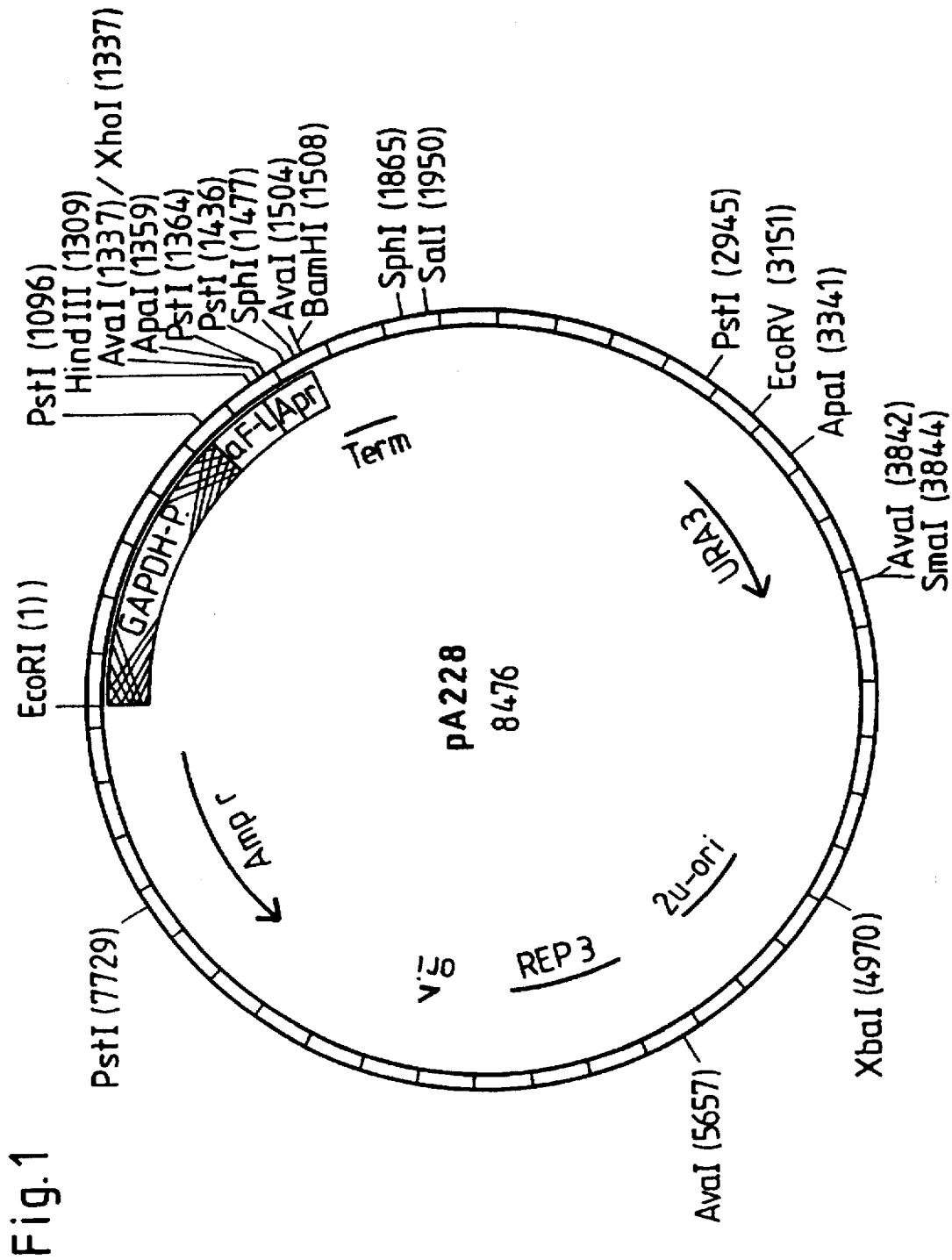
FIG. 1 shows a restriction map of the *E. coli*/yeast shuttle vector pA228. The essential elements of the vector are depicted.

The *E. coli*/yeast shuttle vector pA228 (FIG. 1) was employed for constructing a yeast secretion vector in which the Arg-15 aprotinin sequence is linked directly to the alpha factor pre sequence.

Vector pA228 carries an ampicillin resistance gene (bla) and a URA3 gene as selectable marker genes for *E. coli* and yeast respectively. Additional essential elements of the vector are the Col E1 and the 2µ origins of replication (ori). The REP3 locus is also located in the 2 µ-region. A 1300-bp EcoRI/HindIII fragment carries the GAPDH promoter and the N-terminal prepro sequence of the yeast alpha factor precursor protein (Kurjan and Herskowitz, Cell 30, 933–943, 1982). The recognition site for the KexII protease ("Lys-Arg") was restored within the alpha factor prepro sequence by inserting a modified Arg-15 aprotinin cDNA as a HindIII/BamHI fragment (EP 0 419 878).

At the 3' end of the Arg-15 aprotinin sequence, the vector carries a BamHI/SalI fragment from the yeast URA3 gene which in this position functions as the termination signal for transcription (Yarger et al., Mol. Cell. Biol. 6, 1095–1101, 1986).

The vector pA228 was cut with the restriction endonucleases EcoRI and BamHI. The resulting 1500-bp DNA fragment, which carries the sequence information for the GAPDH promoter, the alpha factor prepro sequence and the Arg-15 aprotinin gene, was cloned into vector M13mp19 which had likewise been cut with EcoRI and BamHI. Single-stranded DNA was prepared and subjected to deletion mutagenesis using the following oligonucleoide:

5' GCAGCATCCTCCGCATTAGCTCGTCCG-GACTTCTGCCTCGAG 3'

Figure 2:
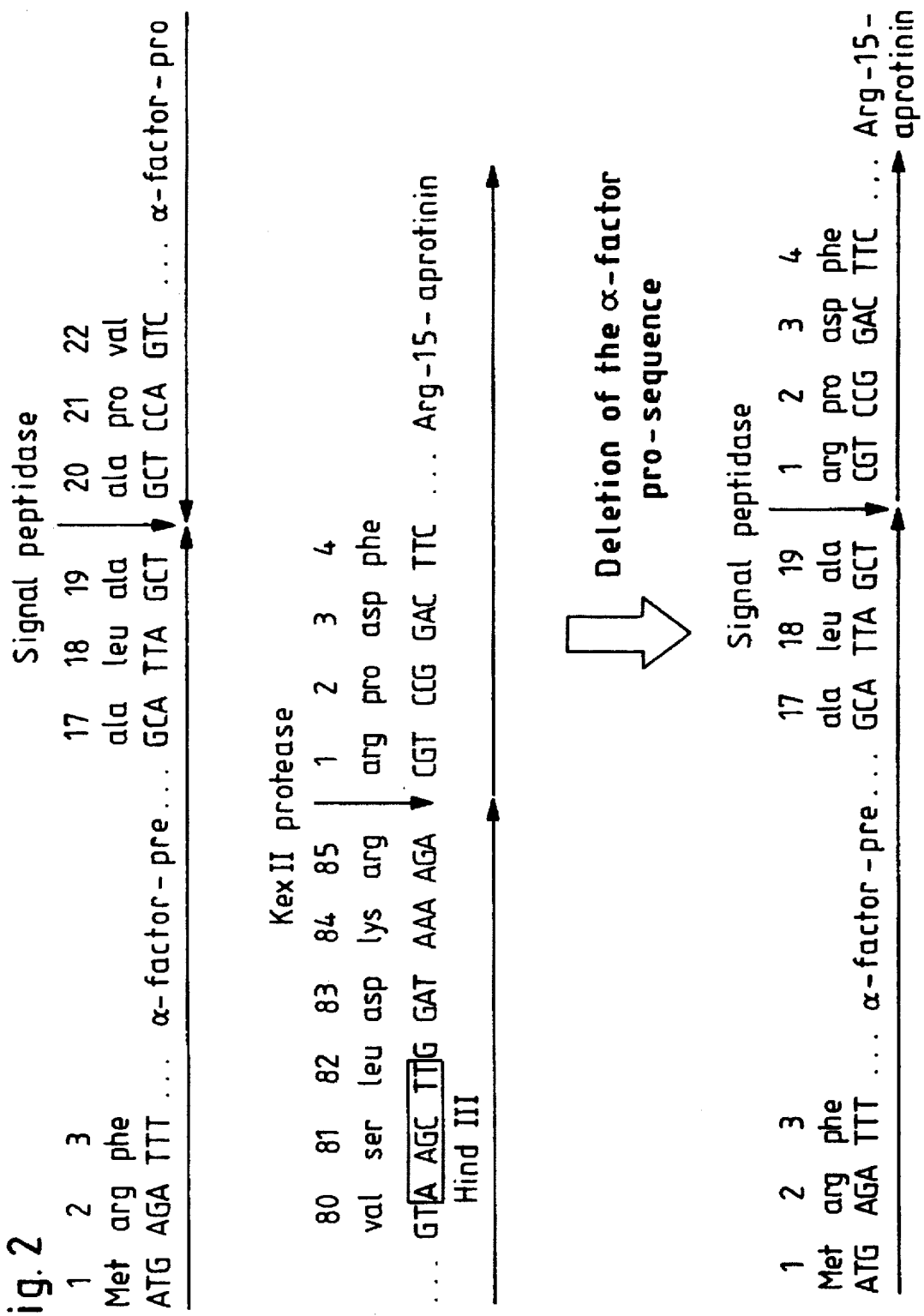
FIG. 2 shows the crucial sequences (nucleotides and amino acids) of the prepro-alpha factor/aprotinin fusion construct before and after deletion of the alpha factor pro sequence. The recognition site for the restriction e endonuclease HindIII and the cleavage sites for the signal peptidase and the KexII protease are also indicated.

The plaques were screened by means of a restriction analysis using double-stranded M13 RF DNA (replicative form). It was possible to identify positive clones by means of restriction digestion using the enzyme HindIII, since a HindIII cleavage site disappears as a result of deleting the alpha factor pro sequence. Deletion of the alpha factor pro sequence, and correct linkage of the alpha factor pre sequence to the Arg-15 aprotinin gene, were also confirmed by sequencing (FIG. 2). A 1300-bp DNA fragment was excised from the selected M13mp19 clone using EcoRI and BamHI, purified by agarose gel electrophoresis, and cloned into vector pA228 which had likewise been cut with EcoRI and BamHI and then gel-purified. Yeast cells (SC125A) were transformed with the vector pAP02 which resulted from this cloning.

Other *E. coli*/yeast shuttle vectors having different promoters, such as, for example, the constitutive MFα1 or the inducible GAL 10 promoter, may be prepared in a similar manner and also result in the secretion of aprotinin and aprotinin variants having a natural N terminus.

In addition, it is also possible to employ shuttle vectors which have different yeast origins of replication, such as, for example, the chromosomal autonomously replicating segment (ars).

Suitable selectable marker genes in addition to the URA3 gene are those genes which help an auxotrophic yeast mutant to become prototrophic, such as, for example, the LEU2, HIS3 or TRP1 genes. Of course, genes may also be employed whose products mediate resistance to various antibiotics, such as, for example, the aminoglycoside G418.

It is not only in the yeast *Saccharomyces cerevisiae* that it is possible to express aprotinin and aprotinin variants having the natural N-terminal sequence. Other yeasts, such as, for example, *Schizosaccharomyces pombe* or the methylotrophic yeasts *Pichia pastoris* and *Hansenula polymorpha*, are also suitable for this purpose.

In addition to the pre alpha-factor signal sequence, other signal sequences, such as, for example, the phosphatase (PHO1 and PHO5) and the invertase signal sequences, may also be used, insofar as it is only the signal peptidase which is required for the processing.

Example 2

Expression of Aprotinin and Aprotinin Variants having the Natural N-terminal Amino Acid Sequence using Constitutive Promoters Yeast transformants harbouring the pAP02 vector or an analogue of this vector having a constitutive promoter (e.g. alpha-mating factor (MFα1) promoter, GAPDH promoter or TPI promoter) were cultivated at 28° C. on a 10-litre scale. During the fermentation, the product was quantified using the elastase inhibition test (when Val15 aprotinin, Val15-Leu17 aprotinin or Val15-Leu17-Arg19 aprotinin were being expressed) or using the trypsin inhibition test (when aprotinin, Arg15 aprotinin or Arg15-Ala17 aprotinin were being expressed). The fermentation lasted 96 hours. The biomass concentration achieved at the end of the fermentation was 31 g dry weight/l. The concentration of the product was about 10 mg/l. After separating off the cells by centrifugation (15 min. 6,500×g, 4° C.) and sterilizing by filtration, the product was purified from the cell-free culture broth.

Example 3

Expression of Aprotinin and Aprotinin Variants having a Natural N-terminal Amino Acid Sequence using Inducible Promoters Yeast transformants harbouring an analogue of the pAP02 vector having an inducible promoter (e.g. Gal10 promoter or a derivative of the Gal10 promoter) were cultivated at 28° C. on a 10-litre scale. After a fermentation period of 48 hours, induction was carried out by changing the carbohydrate used in the feed solution from glucose to galactose. During the fermentation, the product was quantified using the elastase inhibition test (when Val15 aprotinin, Val15-Leu17 aprotinin or Val15-Leu 17-Arg 19 aprotinin were being expressed) or using the trypsin inhibition test (when aprotinin, Arg15 aprotinin or Arg15-Ala17 aprotinin were being expressed). The fermentation lasted 96 hours. The concentration of biomass achieved at the end of the fermentation was 24 g dry weight/l; the concentration of product achieved was about 15 mg/l. After separating off the cells and sterilizing by filtration, the product was purified from the cell-free culture broth.

In analogy with this process, other inducible promoters may also be employed to express aprotinin or aprotinin variants having a natural N-terminal amino acid sequence. A suitable induction technique must be employed which depends on the nature of the chosen promoter.

Example 4

Purification of a Recombinant Aprotinin Variant 5 litres of fermentation supernatant were adjusted to pH 3.0 by adding 150 ml of citric acid. 200 ml of SP-Sepharose-FF gel (Pharmacia), equilibrated with 50 mM sodium citrate, pH 3.0, were added and the whole mixture was stirred at room temperature for 45 minutes. The gel was washed with 50 mM sodium citrate, pH 3.0, and used to fill a column. The column was washed consecutively with 50 mM sodium titrate, pH 3.0, 50 mM TRIS, pH 9.0, and 20 mM HEPES, pH 6.0. The bound material was eluted batchwise using 0.25M, 0.55M and 1M NaCl in 20 mM HEPES, pH 6.0. Fractions in which trypsin inhibitor activity was found were combined and adjusted to pH 3.0 using citric acid. Water was added to reduce conductivity (final value≦17.5 mS/cm). The material was then loaded onto a 100 ml S-Sepharose-HP column (Pharmacia) which was equilibrated with 50 mM sodium citrate, pH 3.0. The product was eluted with a linear NaCl gradient (0–1M NaCl in 20 mM HEPES, pH 6.0). Fractions in which trypsin inhibitor activity was found were combined, dialysed against 50 mM NH$_4$HCO$_3$ and then lyophilized.

Example 5

Characterization of the Isolated Aprotinin Variant

The lyophilized material was characterized by determining the N-terminal amino acids (FIG. 3) and by analysing the amino acid composition (FIG. 4). No other aprotinin sequences were detectable apart from the aprotinin variant having the correctly processed N terminus.

TABLE

Amino acid composition of a purified Arg-15 aprotinin variant having the correctly processed, natural N terminus

| Amino acid | Theoretical value | Factorized amino acid |
|---|---|---|
| CYS | 6 | 4.83 |
| ASP | 5 | 5.00 |
| THR | 3 | 2.72 |
| SER | 1 | 1.02 |
| GLU | 3 | 3.30 |
| GLY | 6 | 6.14 |
| ALA | 6 | 5.99 |
| VAL | 1 | 0.90 |
| MET | 1 | 0.72 |
| ILE | 2 | 1.43 |
| LEU | 2 | 1.83 |
| TYR | 4 | 3.71 |
| PHE | 4 | 4.06 |
| HIS | — | 0.12 |
| LYS | 3 | 3.61 |
| ARG | 7 | 7.02 |
| PRO | 4 | 3.70 |
| TRP | — | n.d. |

---

We claim:

1. A vector for expressing in yeast cells aprotinin and aprotinin variants having a correct N terminus, said vector comprising:

a) the gene for the aprotinin or the variant, and b) as a leader directly upstream of this gene, the nucleotide sequence for the yeast a Mating Factor signal sequence.

2. A process for preparing aprotinin and aprotinin variants having a correct N terminus, said process comprising:

a) culturing yeast cells expressing the vector according to claim 1; and b) isolating the aprotinin or aprotinin variant from the culture supernatant.

* * * * *

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: no ( i v ) ANTI-SENSE: no ( x i ) SEQUENCE DESCRIPTION: SEQ ID NO:1:

GCAGCATCCT CCGCATTAGC TCGTCCGGAC TTCTGCCTCG AG    42

( 2 ) INFORMATION FOR SEQ ID NO: 2:

( i ) SEQUENCE CHARACTERISTICS:
        ( A ) LENGTH: 234 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: no ( i v ) ANTI-SENSE: no ( x i ) SEQUENCE DESCRIPTION: SEQ ID NO:2:

ATGAGATTTC CTTCAATTTT TACTGCAGTT TTATTCGCAG    40

-continued

| | | | | |
|---|---|---|---|---|
| CATCCTCCGC | ATTAGCTCGT | CCGGACTTCT | GCCTCGAGCC | 80 |
| GCCGTACACT | GGGCCCTGCA | GAGCTCGTAT | CATCCGTTAC | 120 |
| TTCTACAATG | CAAAGGCAGG | CCTGTGTCAG | ACCTTCGTAT | 160 |
| ACGGCGGCTG | CAGAGCTAAG | CGTAACAACT | TCAAATCCGC | 200 |
| GGAAGACTGC | ATGCGTACTT | GCGGTGGTGC | TTAG | 234 |

(2) INFORMATION FOR SEQ ID NO: 3:

(i) SEQUENCE CHARACTERISTICS:
        (A) LENGTH: 77 amino acids
        (B) TYPE: amino acid
        (C) STRANDEDNESS: single
        (D) TOPOLOGY: linear (ii) MOLECULE TYPE: protein (iii) HYPOTHETICAL: no (v) FRAGMENT TYPE: N terminus (xi) SEQUENCE DESCRIPTION: SEQ ID NO:3:

| Met | Arg | Phe | Pro | Ser | Ile | Phe | Thr | Ala | Val | Leu | Phe | Ala |
|---|---|---|---|---|---|---|---|---|---|---|---|---|
| | | | | 5 | | | | | 10 | | | |
| Ala | Ser | Ser | Ala | Leu | Ala | Arg | Pro | Asp | Phe | Cys | Leu | Glu |
| 15 | | | | | | 20 | | | | | 25 | |
| Pro | Pro | Tyr | Thr | Gly | Pro | Cys | Arg | Ala | Arg | Ile | Ile | Arg |
| | | | 30 | | | | | 35 | | | | |
| Tyr | Phe | Tyr | Asn | Ala | Lys | Ala | Gly | Leu | Cys | Gln | Thr | Phe |
| 40 | | | | | 45 | | | | | 50 | | |
| Val | Tyr | Gly | Gly | Cys | Arg | Ala | Lys | Arg | Asn | Asn | Phe | Lys |
| | | 55 | | | | | 60 | | | | | 65 |
| Ser | Ala | Glu | Asp | Cys | Met | Arg | Thr | Cys | Gly | Gly | Ala | |
| | | | | 70 | | | | | 75 | | | |

(2) INFORMATION FOR SEQ ID NO: 4:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (iii) HYPOTHETICAL: no (v) FRAGMENT TYPE: N terminus (xi) SEQUENCE DESCRIPTION: SEQ ID NO:4:

| Arg | Pro | Asp | Phe | Cys | Leu | Glu | Pro | Pro | Tyr | Thr | Gly | Pro |
|---|---|---|---|---|---|---|---|---|---|---|---|---|
| | | | | 5 | | | | | 10 | | | |
| Cys | Arg | Ala | Arg | Ile | Ile | | | | | | | |
| | 15 | | | | | | | | | | | |